(12) United States Patent
Rodolfi et al.

(10) Patent No.: US 11,123,579 B2
(45) Date of Patent: *Sep. 21, 2021

(54) DETERGENT PRODUCT FOR COSMETIC USE

(71) Applicant: COMPA S.C. a.r.l., Ferrara (IT)

(72) Inventors: Alberto Rodolfi, Cento (IT); Elisabetta Caselli, Ferrara (IT)

(73) Assignee: COPMA S. C. A. R. L., Ferrara (IT)

( * ) Notice: Subject to any disclaimer, the term of this patent is extended or adjusted under 35 U.S.C. 154(b) by 189 days.

This patent is subject to a terminal disclaimer.

(21) Appl. No.: 16/334,623

(22) PCT Filed: Sep. 21, 2017

(86) PCT No.: PCT/IB2017/055740
§ 371 (c)(1),
(2) Date: Mar. 19, 2019

(87) PCT Pub. No.: WO2018/055553
PCT Pub. Date: Mar. 29, 2018

(65) Prior Publication Data
US 2020/0038316 A1 Feb. 6, 2020

(30) Foreign Application Priority Data
Sep. 22, 2016 (IT) .................. 102016000095070

(51) Int. Cl.
| | | |
|---|---|---|
| *A61K 8/99* | (2017.01) | |
| *A61Q 19/10* | (2006.01) | |
| *A61K 8/19* | (2006.01) | |
| *A61K 8/34* | (2006.01) | |
| *A61K 8/46* | (2006.01) | |
| *A61K 8/81* | (2006.01) | |
| *A61Q 3/00* | (2006.01) | |
| *A61Q 5/02* | (2006.01) | |
| *A61Q 11/00* | (2006.01) | |
| *A01N 63/40* | (2020.01) | |

(52) U.S. Cl.
CPC ............. *A61Q 19/10* (2013.01); *A01N 63/40* (2020.01); *A61K 8/19* (2013.01); *A61K 8/345* (2013.01); *A61K 8/463* (2013.01); *A61K 8/8147* (2013.01); *A61K 8/99* (2013.01); *A61Q 3/00* (2013.01); *A61Q 5/02* (2013.01); *A61Q 11/00* (2013.01)

(58) Field of Classification Search
CPC .......... C11D 3/381; C11D 1/38; A61Q 19/10; A61K 8/19
See application file for complete search history.

(56) References Cited

U.S. PATENT DOCUMENTS

| | | | |
|---|---|---|---|
| 6,387,874 B1 | 5/2002 | Schalitz et al. | |
| 2007/0054357 A1* | 3/2007 | Pasternack | C12Q 1/701 435/69.1 |
| 2011/0318289 A1 | 12/2011 | Frodyma et al. | |

FOREIGN PATENT DOCUMENTS

| | | |
|---|---|---|
| EP | 0414304 A2 | 2/1991 |
| GB | 2484134 A | 4/2012 |
| WO | 2016170479 A1 | 10/2016 |

OTHER PUBLICATIONS

Dias et al., The use of phage: Therapy, biocontrol and commercial microbiology, p. 1-35. (Year: 2013).*

* cited by examiner

*Primary Examiner* — Taeyoon Kim
*Assistant Examiner* — Tiffany M Gough
(74) *Attorney, Agent, or Firm* — Henry D. Coleman; R. Neil Sudol

(57) ABSTRACT

The detergent product for cosmetic use, comprises: a base compound having a detergent action; spores of probiotic bacteria mixed with the base compound; bacteriophage elements mixed with the base compound and having bactericide activity on predetermined undesired bacterial species present, the bacteriophage elements, in cooperation with the spores of probiotic bacteria, being able to carry out a combined and synergic action against damaging microorganisms. Use of the detergent product is also described, for cleansing of the skin, skin adnexa (hair, nails, body hair, beard), of the oral cavity, mucosa or the teeth.

8 Claims, 5 Drawing Sheets

DETERGENT PRODUCT FOR COSMETIC USE

FIELD OF THE INVENTION

The present invention relates to the technical sector relating to cosmetic treatments for topical use, in the field of detergents.

There is at present a progressively growing demand for products for cleansing and caring for the skin and its adnexa (hair, keratin fibres, body hair, nails, beard) of the oral cavity, the mucosa and the teeth, based on natural, non-allergenic and biological formulations.

DESCRIPTION OF THE PRIOR ART

Many of the products at present on the market for the cleansing/sanitising of the skin are based on the presence of chemical and/or pharmacological additives, which have the aim of preventing the onset of infections/inflammation, or of facilitating the restoring of the skin functions following the development of infections/inflammation of the skin and the adnexa.

It is known that the skin and its adnexa (hair, keratin fibres, body hair, nails, beard), the oral cavity, mucosa and teeth, are colonised by numerous micro-organisms (especially bacteria and fungi), which in their entirety form the cutaneous commensal microbiota.

However, the presence of some types of micro-organisms on the skin, the oral cavity, the mucosa and teeth, can constitute a risk for development of infections or inflammations.

As the presence of benign non-pathogenic micro-organisms effectively opposes colonisation by potentially pathogenic micro-organisms, the Applicant notes that there already exist detergent products on the free market, under the name of BI-SAFE® (Probiotic Hygiene and Care Hand Soap, Chrisal), which contain probiotic bacteria of the *Bacillus* genus, with the aim of limiting the use of chemical disinfectants and facilitating a benign colonisation of the skin, so that the skin can combat pathogenic micro-organisms and render their population difficult.

These products exploit a "biocontrol" approach based on the fact that the probiotic micro-organisms (non-pathogens) can colonise the skin and the adnexa, competing with the proliferation of other species that are potentially risky for the health of individuals.

The bacteria of the *Bacillus* genus represent a vast group of spore-forming Gram-positive bacteria, ubiquitous in nature and also present in the human intestine.

The spores formed by the *Bacillus* bacteria can survive for very long times, because of their resistance to desiccation, heat and many chemical substances, and are therefore ideal for probiotic applications in the field of cosmetics.

It is also noteworthy that from the point of view of safety, the *Bacillus* species present in the products used are considered low/null risk for pathogens (non-pathogenic).

The presence of the probiotics further prevents re-colonisation by contaminant micro-organisms, thus stably maintaining the hygiene where the probiotics are applied.

As this is a system based on the biological mechanism of competitive antagonism between probiotics and contaminant microbes, it can however be necessary to make prolonged use in order to reach the stable destruction of the potentially harmful microbial load.

SUMMARY OF THE INVENTION

An aim of the present invention is to obviate the above drawbacks by providing a detergent product for cosmetic use able to act rapidly and effectively against any potentially-dangerous microbial species, including those of the multi-resistant type (superbugs).

The above-indicated aims are obtained by a cosmetic product realised according to claim 1, and a use of the cosmetic product according to claim 10.

In particular embodiments, the product for cosmetic use comprises the following compounds, in combination:
- the base compound can be in the solid, liquid or gaseous state;
- the base compound can comprise at least cationic surfactants, anionic surfactants or amphoteric compounds or mixtures thereof;
- the base compound can comprise: PEG-6-caprylic/capric glycerides; Sodium laureth sulfate; Sodium lauryl sulfate; Acrylates/steareth-20 methacrylate copolymer; phenoxyethanol; ethylhexylglycerin, potassium hydroxide;
- the probiotic bacteria spores are mixed with the base compound at a concentration comprised between $10^2$-$10^9$ spores/ml;
- the bacteriophage elements are mixed with the base compound at a concentration comprised between $10^3$-$10^9$ PFU/ml;
- the probiotic bacteria are of the *Bacillus* genus (preferably though not exclusively of the species *Bacillus subtilis*, *Bacillus megaterium* and *Bacillus pumilus*);
- the bacteriophage elements comprise bacteriophages of the family Caudovirales and/or of the family Microviridae and/or of the family Leviviridae and/or of the family Inoviridae and/or of the family Tectiviridae and/or of the family Corticoviridae;

The characteristics of the invention are specified in the following in which some preferred, but not exclusive, embodiments are described.

BREVE DESCRIPTION OF THE DRAWINGS

Figure 1:
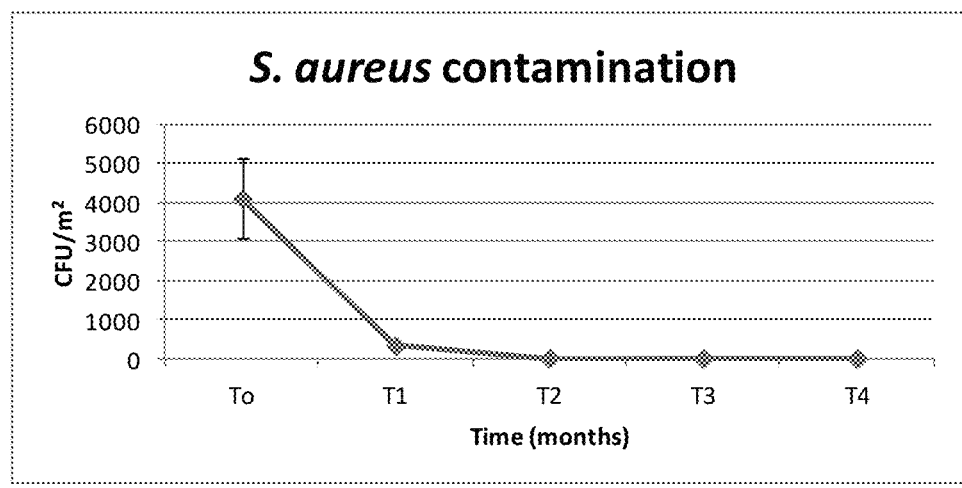
FIGS. 1-3 are graphs relating to colonisation over time, respectively to *Staphylococcus aureus*, Enterobacteriaceae spp. Gram negative) and *Candida albicans*, on surfaces treated with probiotic bacteria.

The proposed detergent product for cosmetic use innovatively comprises:
- a base compound having a detergent action;
- spores of probiotic bacteria mixed with the base compound;
- bacteriophage elements mixed with the base compound and having bactericide activity on predetermined undesired bacterial species present, the bacteriophage elements, in cooperation with the spores of probiotic bacteria, being able to carry out a combined and synergic action against damaging micro-organisms.

The field of the invention also includes the use of the detergent product for cosmetic use for cleansing of the skin, skin adnexa (hair, body hair, keratin fibres, nails, beard), of the oral cavity, mucosa (in particular of the oral cavity) and the teeth. It is particularly advantageous for the cleansing of the skin, skin adnexa, hair, nails, body hair, beard, for external intimate hygiene.

The base compound can comprise one or more of the following: PEG-6-caprylic/capric glycerides; Sodium laureth sulfate; Sodium lauryl sulfate; Acrylates/steareth-20 methacrylate copolymer; phenoxyethanol; ethylhexylglycerin, potassium hydroxide. To these can also be added cocamidopropyl betaine and dodecyl-betaine.

The spores of probiotic bacteria can be present in the detergent product of the invention, at a concentration comprised between $10^2$-$10^9$ spore/ml, preferably from $10^5$-$10^9$ spore/ml, more preferably $10^6$-$10^8$ spore/ml.

The bacteriophage elements specifically directed against bacteria potentially able to cause infection/inflammation of the skin or adnexa can be present in the detergent product of the invention, at a concentration comprised between $10^3$-$10^9$ spore/ml, preferably from $10^5$-$10^9$ spore/ml, more preferably $10^6$-$10^8$ spore/ml.

By way of non-limiting example, the probiotic bacteria can be of the *Bacillus* genus, including the species *Bacillus subtilis*, *Bacillus megaterium* and *Bacillus pumilus*.

This does not exclude the possibility that further probiotic bacteria can be used, as a function of the undesired bacterial species to be compared and contrasted.

The bacteriophage element can advantageously be selected, alternatively or in combination, according to the bacterial species to be compared, from among the following families: Caudovirales, Microviridae, Leviviridae, Inoviridae, Tectiviridae, Corticoviridae.

As is known, the bacteriophage elements of the Caudovirales family also comprise the Myoviridae, Siphoviridae, Podoviridae families.

The detergent product of the invention for cosmetic use, in the preferred embodiments as indicated in the foregoing, is particularly suitable for cleansing of the skin, skin adnexa (hair, body hair, keratin fibres, nails), the oral cavity, the mucosa (in particular of the oral cavity) and teeth.

It can be produced in the solid state (for example for soaps, powders etc.) or in the liquid state (for example creams, lotions, gels, foams etc.) or in the gaseous state (for example for sprays etc.) or an emulsion or a suspension or a paste (for example a toothpaste).

The detergent product for cosmetic use can be advantageously a toothpaste, a soap, a beauty soap, a deodorant soap, a depilating soap, a shaving soap or foam, a make-up removing product for the face and/or eyes (for example a detergent milk, micellar water, tonic), a foam bath, a shower bath, an intimate detergent for external use, a liquid shampoo, a powder shampoo, a hair conditioner balsam, a deodorant, an anti-perspirant product, or a bath salt. Preferably the detergent product for cosmetic use is a toothpaste, a soap, a beauty soap, a deodorant soap, a depilating soap, a shaving soap or foam, a make-up removing product for the face and/or eyes (for example a detergent milk, micellar water, tonic), a foam bath, a shower bath, an intimate detergent for external use, a liquid shampoo, or a powder shampoo. In particular, bath and/or shower products can be in liquid form, such as a liquid detergent product, a foam, oils, gels, or they can be in the form of salts and are preferably a liquid detergent, and oil or a gel.

In a preferred embodiment of the invention, the detergent product for cosmetic use of the invention is a product for shaving such as, for example, a shaving cream, foam or lotion, or a depilating soap, and more preferably it is a cream, a shaving foam or a depilating soap. Note that where there is a beard or profuse body hair there is a greater colonisation of numerous micro-organisms and a tendency to inflammation of the shaven and/or depilated skin and that the shaving creams or foams and the depilating soaps of known type comprise a base compound having a detergent activity and in fact once rinsed they cleanse the skin and the adnexa.

Therefore the use of the detergent product for cosmetic use according to the invention for shaving or depilation is preferred.

In a further aspect of the invention, the detergent product for cosmetic use of the invention is a product for oral hygiene, in particular a toothpaste, in particular if in paste, gel or powder form. The use thereof for cleaning the teeth and/or the mucous membranes of the oral cavity is consequently advantageous.

In a further embodiment of the detergent product of the invention, the detergent product for cosmetic use of the invention is a make-up removal detergent for the face and/or eyes. It is consequently advantageous to use the product for cleansing the face and/or the eyes of make-up.

The action of the bacteriophages is specific, as specific types of lithic bacteriophages kill specific types of bacteria, and therefore perform a potentially very effective and specific action in the direct battle against undesired bacteria.

It is further evidenced how the use of specific bacteriophages prevents the risk of damage to the probiotic *Bacillus*, which can therefore be kept intact and effective in their activity.

The use of bacteriophages in detergent products for cosmetic use is particularly indicated as they are rather stable in differing temperature conditions, pH and salinity of the environment, and can therefore be added to base compounds without suffering in terms of activity and without the base compound losing detergent activity.

As the Applicant is not at present empowered to carry out laboratory testing on animals or human beings, it has used alternative methods to carry out experimental testing on inert surfaces.

These laboratory test give evidence of the synergic effect deriving from the combined use of probiotic bacteria and bacteriophage elements with respect to the single use of probiotic bacteria or bacteriophage elements.

Test n° 1 (Use Only of Probiotic Bacteria)

The activity of PCHS detergents containing probiotics has been amply evaluated on inert surfaces, where they have shown themselves to be able to destroy the microbial load by about 90% more with respect to traditional detergents, with protracted use for about one month.

After a period of two months destruction, the contaminant load is stably low regarding both the bacteria and the fungi [Caselli et al., 2016].

Figure 2:
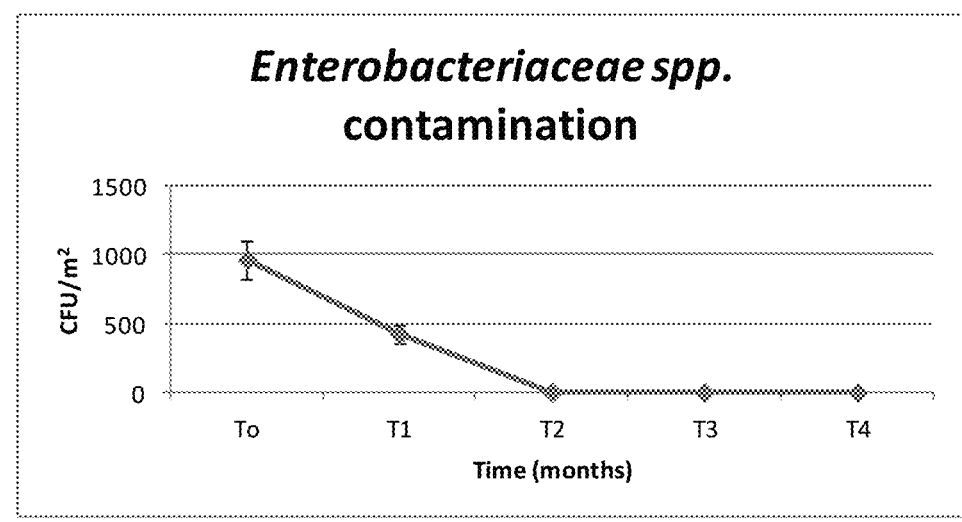
Figure 3:
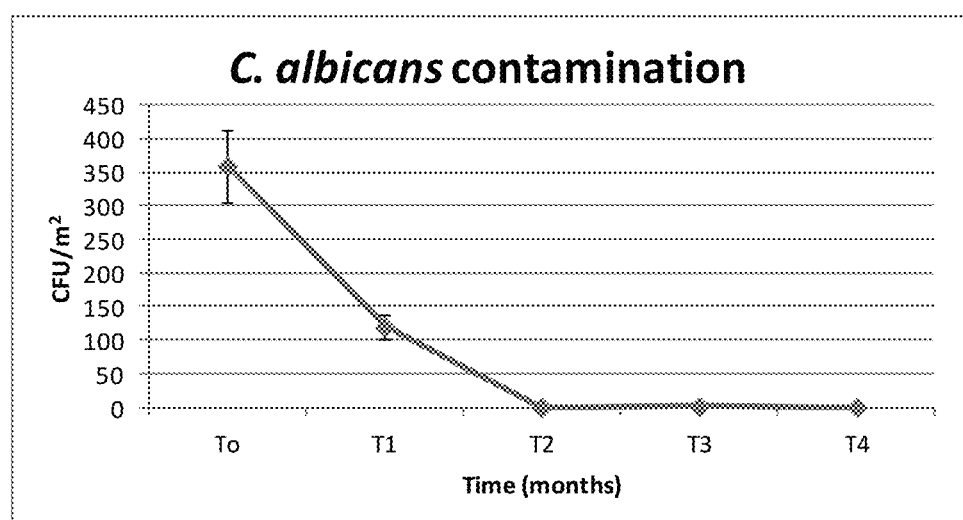

FIGS. 1-3 illustrate the antimicrobial action (bacteria and fungi) of detergent product based only on probiotics.

The trend of contamination by *Staphylococcus aureus* (taken as an example of Gram positive bacteria), Enterobacteriaceae spp. (as an example of Gram negative bacteria) and *Candida albicans* (as an example of fungi), was measured on the field, with application of Rodac plates of specific media for the indicated bacteria and fungi species.

Test n° 2 (Use Only of Bacteriophages)

Figure 4:
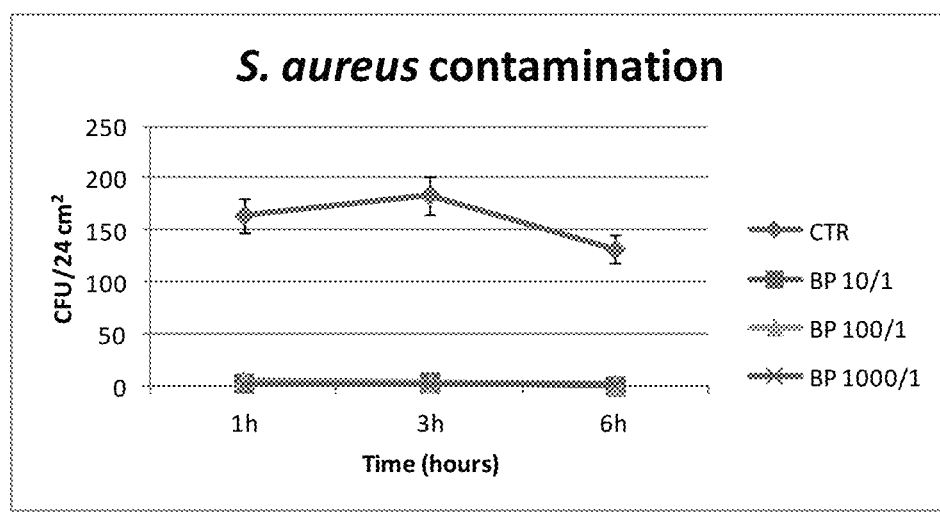
FIGS. 4-6 are graphs relating to colonisation over time, respectively to *Staphylococcus aureus*, Enterobacteriaceae spp. Gram negative) and *Candida albicans*, on surfaces treated with bacteriophages.
Figure 5:
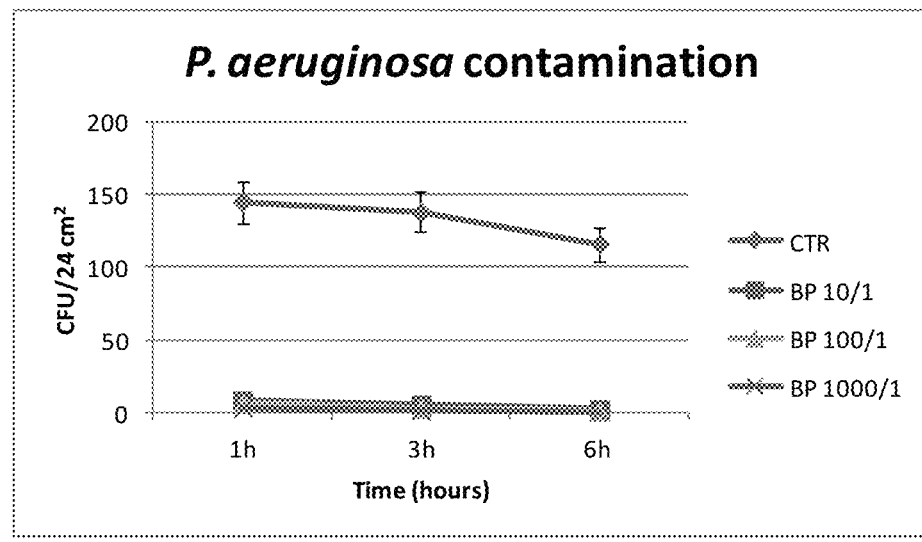
Figure 6:
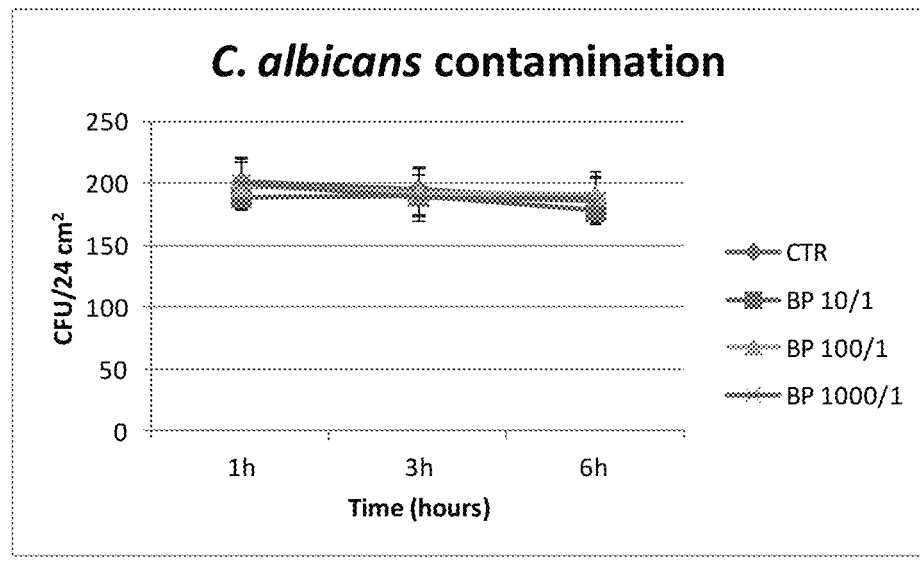

FIG. 4-6 illustrate the anti-bacterial action of the bacteriophages on an inert surfaces contaminate by specific target bacteria.

The trend of contamination by *Staphylococcus aureus* (taken as an example of Gram positive bacteria), *Pseudomonas aeruginosa* (as an example of Gram negative bacteria) and *Candida albicans* (as an example of fungi), was measured in vitro, on experimental models of inert surfaces having an area of 24 $cm^2$.

The surfaces were contaminated with a known quantity of micro-organism ($10^2$ CFU/24 $cm^2$) and then treated by application of growing concentrations of specific bacteriophages (respectively $10^3$, $10^4$, $10^5$ PFU), therefore in ratios of 10:1, 100:1 and 1000:1 with the seeded target bacteria.

For the fungi a combination of the bacteriophages used against the Gram positive and Gram negative bacteria was used.

The residual contamination was evaluated after 1, 3, 6 hours by application of Rodac plates of specific medium for the indicated bacterial and fungi species.

The results are expressed as mean values±S.D. of samples in duplicate in three independent experiments.

It can be noted that already after one hour, and at the lower concentration, the bacteriophages are able to remove more than 90% of the bacterial cells against which they are specifically directed.

The treatment with only bacteriophages has the limitation of being directed only against the bacteria specifically recognised by the bacteriophages, and therefore in a case of contamination by bacterial species different from those against which the bacteriophages are specifically directed, the surface treated is contaminated by the species not attacked by the bacteriophages, as the bacteriophages are by definition specific for a bacterial species, and therefore not able to attack other bacterial species, not are they able to attack species of fungi.

These limitations of the bacteriophages are overcome by the addition of the probiotics, which instead have a slower action, but generalised and independent of the bacterial or fungi species present.

Test n° 3 (Combined Use of Probiotic Bacteria/Bacteriophages)

Figure 7:
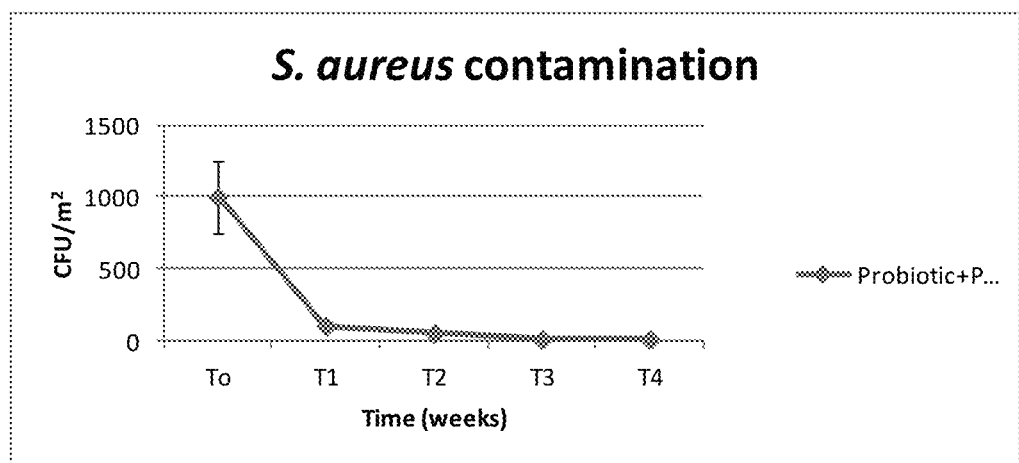
FIGS. 7-9 are graphs relating to colonisation over time, respectively to *Staphylococcus aureus*, Enterobacteriaceae spp. Gram negative) and *Candida albicans*, on surfaces treated with bacteriophages and with probiotic bacteria.
Figure 8:
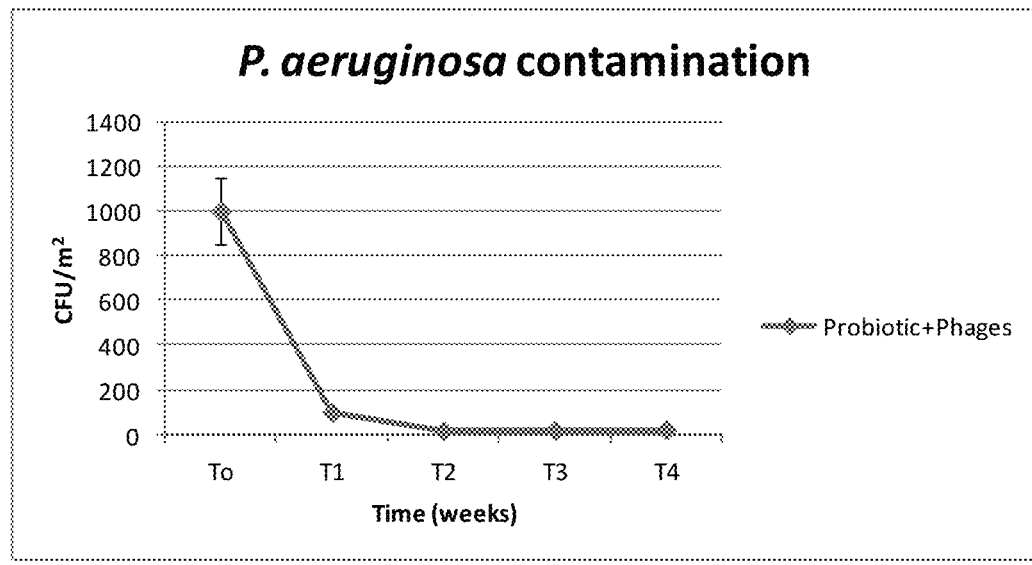
Figure 9:
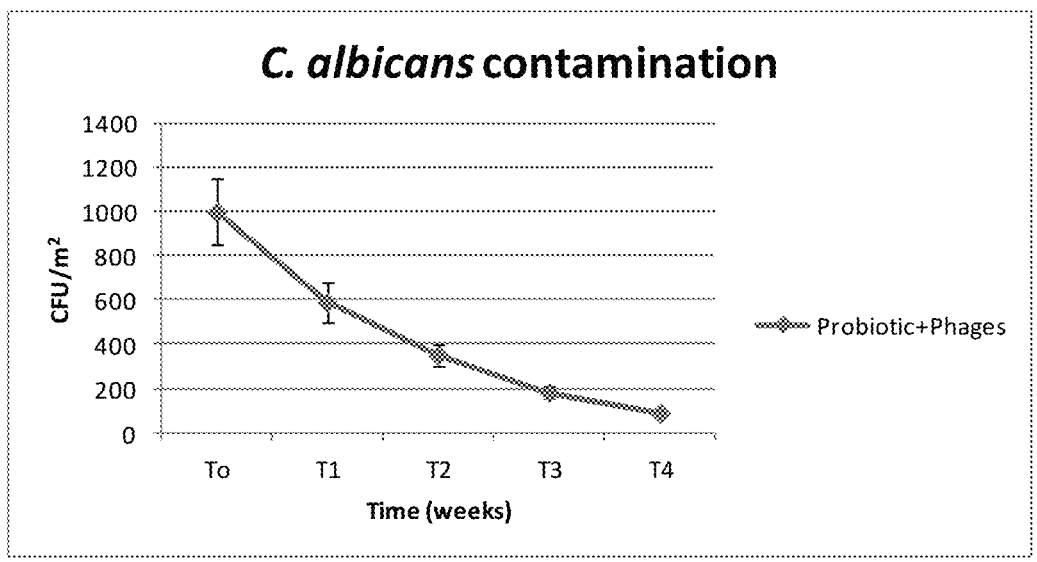

FIGS. 7-9 illustrate the effect of the combined and synergic antimicrobial action obtained with the contemporary presence of probiotic bacteria and bacteriophages on surfaces contaminated by the specific microbes illustrated.

The trend of contamination by *Staphylococcus aureus* (taken as an example of Gram positive bacteria), *Pseudomonas aeruginosa* (as an example of Gram negative bacteria) and *Candida albicans* (as an example of fungi), was measured in vitro, on experimental models of inert surfaces of non-porous and sterile material having an area of 24 $cm^2$.

The surfaces were contaminated with a known quantity of micro-organism ($10^3$ CFU/24 $cm^2$) and then treated by application of a solution containing probiotic bacteria growing concentrations of ($10^3$ CFU/ml) and specific bacteriophages ($10^4$ PFU/ml).

For the fungi a combination of the bacteriophages used against the Gram positive and Gram negative bacteria was used.

The residual contamination was evaluated after 1, 2, 3 and 4 hours by application of Rodac plates of specific medium for the indicated bacterial and fungi species. The results are expressed as mean values±S.D. of samples in duplicate in three independent experiments.

Comparison of the Tests Carried Out

Figure 10:
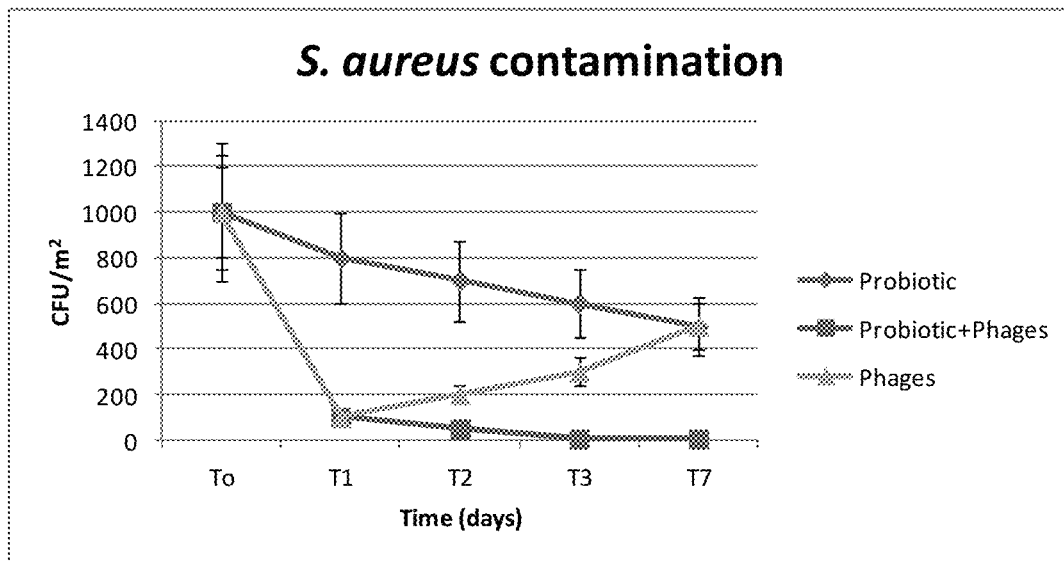
FIG. 10 is a graph relating to colonisation over time, with respect to *Staphylococcus aureus* on surfaces treated with probiotic bacteria and with bacteriophages, with respect to surfaces treated only with probiotic bacteria and only with bacteriophages.

FIG. 10 illustrates the direct comparison between the antimicrobial action of the no. 3 treatments on the contamination by *Staphylococcus aureus*, measured in vitro on experimental models of inert surfaces of 24 $cm^2$.

The surfaces were contaminated with a known quantity of micro-organism ($10^3$ CFU/24 $cm^2$) and then treated by application of a solution containing probiotic bacteria growing concentrations of ($10^3$ CFU/ml), only specific bacteriophages ($10^4$ PFU/ml), or the combination of probiotics and bacteriophages at the indicated concentrations.

The residual contamination was evaluated after 1, 2, 3 and 7 hours by application of Rodac plates of specific medium for *Staphylococcus aureus*.

The results are expressed as mean values±S.D. of samples in duplicate in three independent experiments.

From the experimental tests carried out, it can easily be noted how the contemporaneous presence of *Bacillus* probiotics and anti-pathogen bacteriophages significantly increases the effectiveness of the detergent product for cosmetic use, thanks to the synergic action carried out against the various damaging micro-organisms.

On the one hand the bacteriophages destroy the contaminant load extremely rapidly, but have a limited action over time and do not succeed in preventing re-contamination, nor can they attack bacterial species that are different from those specifically recognised.

On the other hand the probiotics reduce the contaminant load slowly but constantly, thanks to the competitive mechanisms, inhibiting the recontamination and with an action that is independent of the microbial species present.

The contemporaneous presence of probiotics and bacteriophages guarantees the rapidity of the specific antimicrobial action and contemporaneous inhibition of recontamination, ensuring destruction of the pathogen that is rapid and stable over time.

The realising of a product for cosmetic use containing at the same time *Bacillus* probiotics and anti-pathogen bacteriophages has the obvious advantage, with respect to traditional products, of ensuring and extremely rapid and immediate destruction of the contaminant bacterial load.

This is thanks to the combined action performed by the bacteriophages which are able, in a few hours, to kill the target bacteria, and by the probiotic bacteria, which are able to persistently colonise the cutaneous surface, replacing the pathogens.

The presence of the bacteriophages thus represents an empowering of the anti-bacterial action of the product bases on only probiotic *Bacillus* as it facilitates and increases the action of the probiotics, which are also active on fungi.

This guarantees an immediate sanitising effect during the initial step of the cosmetic treatment, enabling the probiotic bacteria to maintain a stably low presence over time of potentially pathogenic bacteria.

The addition of specific bacteriophage elements to the base compound mixed with spores of probiotic *Bacillus* advantageously enables using the product in a directed way, responding to specific needs and/or situations of particular interest, such as for example the destruction of one or more specific bacterial species that are particularly prevalent and/or damaging.

The presence in the product of the invention of a greater number of families of bacteriophage families (Caudovirales, Microviridae, Leviviridae, Inoviridae, Tectiviridae and Corticoviridae) enables the product itself to have a bactericide activity on a broader group of treatable bacterial species.

The predetermined families of bacteriophage elements can be present in the product that is the object of the invention, both singly and in combination, so as to include the possibility of diversified treatments according to the specific need.

From the above it is clear that the detergent product for cosmetic use of the invention is able to active in a particularly rapid and effective way against any potentially-dangerous microbial species, including those of the multi-resistant type (superbugs). The product is particularly effective for cosmetic treatment of the skin and skin adnexa, hair, nails, and the oral cavity, mucosa or teeth, i.e. for cleansing thereof.

The invention claimed is:

1. A detergent product for cosmetic use, comprising:
   a base compound having a detergent action selected from the group consisting of PEG-6-caprylic/capric glycerides, sodium laureth sulfate, sodium lauryl sulfate, acrylates/steareth-20 methacrylate copolymer, phenoxyethanol, ethylhexylglycerin, potassium hydroxide or a mixture thereof;
   spores of probiotic bacteria of the *Bacillus* genus mixed with the base compound wherein the spores are at a concentration of $10^3$ PFU/ml; and
   bacteriophage elements selected from the group consisting of Caudoverales family, Microviridae family, Leviviridae family, Inoviridae family, Tectiviridae family, Corticoviridae family and mixtures thereof mixed with the base compound at a concentration of $10^4$ PFU/ml and having bactericide activity on predetermined undesired bacterial species present, the bacteriophage elements, in cooperation with the spores of probiotic bacteria, providing a synergistic action against damaging micro-organisms.

2. The product of claim 1, wherein the base compound is in a solid, liquid or gaseous state.

3. The product of claim 1, wherein the probiotic bacteria are of a species selected from the group consisting of *Bacillus subtilis, Bacillus megaterium* and *Bacillus pumilus*.

4. The product according to claim 1 which is formulated as a toothpaste, a soap, a beauty soap, a deodorant soap, a depilating soap, a shaving soap or foam, a make-up removing product for the face and/or eyes, a foam bath, a shower bath, an intimate detergent for external use, a liquid shampoo, a powder shampoo, a hair conditioner balsam, a deodorant, an anti-perspirant product or a bath salt.

5. A method of cleansing a surface of a subject, wherein said surface is skin, skin adnexa, hair, nails, body hair, beard, oral cavity, mucosa or teeth of said subject comprising exposing said surface to the detergent product of claim 1.

6. A method of shaving or removing hair of a subject comprising exposing hair of said subject to a depilation or shaving soap or foam according to claim 4.

7. A method for cleansing make-up from the face and/or the eyes of a subject comprising exposing said face and/or eyes to said make-up removing product of claim 4.

8. A method for cleansing a surface of a subject for external intimate hygiene, wherein said surface is skin, skin adnexa, hair, nails, beard or body hair comprising exposing said surface to the intimate detergent of claim 4.

* * * * *